US012649762B2

(12) United States Patent
Datla et al.

(10) Patent No.: US 12,649,762 B2
(45) Date of Patent: Jun. 9, 2026

(54) SYNTHESIS OF CHOLESTEROL AND VITAMIN D3 FROM PHYTOSTEROLS

(71) Applicant: FERMENTA BIOTECH LIMITED, Thane (West) (IN)

(72) Inventors: Anupama Datla, Thane (West) (IN); Prashant Nagre, Thane (West) (IN); Jagdish Tamore, Thane (IN); Manojkumar Sadanand Prabhu, Thane (IN); Sachin Vasant Kadam, Thane (IN)

(73) Assignee: FERMENTA BIOTECH LIMITED, Thane (West) (IN)

( * ) Notice: Subject to any disclaimer, the term of this patent is extended or adjusted under 35 U.S.C. 154(b) by 1135 days.

(21) Appl. No.: 17/623,461

(22) PCT Filed: Jul. 2, 2020

(86) PCT No.: PCT/IN2020/050576
§ 371 (c)(1),
(2) Date: Dec. 28, 2021

(87) PCT Pub. No.: WO2021/005618
PCT Pub. Date: Jan. 14, 2021

(65) Prior Publication Data

US 2022/0372065 A1 Nov. 24, 2022

(30) Foreign Application Priority Data

Jul. 9, 2019 (IN) ............................. 201921027409

(51) Int. Cl.
*C07J 9/00* (2006.01)
*C07C 401/00* (2006.01)

(52) U.S. Cl.
CPC ............... *C07J 9/00* (2013.01); *C07C 401/00* (2013.01)

(58) Field of Classification Search
CPC ................................ C07J 9/00; C07C 401/00
See application file for complete search history.

(56) References Cited

U.S. PATENT DOCUMENTS

| | | | |
|---|---|---|---|
| 3,822,254 | A | 7/1974 | Partridge et al. |
| 3,920,531 | A | 11/1975 | Mazur et al. |
| 4,686,023 | A | 8/1987 | Stevens |
| 5,128,162 | A | 7/1992 | Wrezel et al. |
| 5,252,191 | A | 10/1993 | Pauli et al. |

FOREIGN PATENT DOCUMENTS

| | | | |
|---|---|---|---|
| WO | 1995014032 | A1 | 5/1995 |
| WO | 2016096988 | A1 | 6/2016 |
| WO | 2016096989 | A1 | 6/2016 |

OTHER PUBLICATIONS

Komba, Simultaneous Synthesis of Vitamins D2, D4, D5, D6 and D7 from Commercially available phytosterol, beta-sitosterol, and identification of each Vitamin D by HSQC NMR, 2019, Metabolites, vol. 9(107), p. 1-12 (Year: 2019).*
Richey et al, Methyl Magnesium Bromide from Encyclopedia of Reagents of Organic Synthesis, 2008, obtained from https://onlinelibrary.wiley.com/doi/epdf/10.1002/047084289X.rm206.pub2, p. 1-5 (Year: 2008).*
International Search Report re: PCT/IN2020/050576 dated Oct. 26, 2020.
Written Opinion of Search Report re: PCT/IN2020/050576 dated Oct. 26, 2020.
Komba et al., "Simultaneous Synthesis of Vitamins D2, D4, D5, D6, and D7 from Commercially Available Phytosterol, β-Sitosterol, and Identification of Each Vitamin D by HSQC NMR," Metabolites 2019, 9(6), 107.
Richey Jr., "Methylmagnesium Bromide," Encyclopedia of Reagents for Organic Synthesis, Wiley Online Library. URL: https://doi.org/10.1002/047084289X.rm206 First Published Apr. 15, 2001.

* cited by examiner

*Primary Examiner* — Adam C Milligan
*Assistant Examiner* — Karen Cheng
(74) *Attorney, Agent, or Firm* — Kramer & Amado, P.C.

(57) ABSTRACT

The present invention discloses novel method for synthesizing vegan cholesterol and vitamin D3 from inexpensive crude phytosterol.

11 Claims, No Drawings

SYNTHESIS OF CHOLESTEROL AND VITAMIN D3 FROM PHYTOSTEROLS

TECHNICAL FIELD

The present invention relates to novel method for synthesizing vegan cholesterol and vitamin D3 from inexpensive crude phytosterols.

BACKGROUND AND PRIOR ART

Cholesterol is a precursor to vitamin D, inhibiting the synthesis of cholesterol will also inhibit the synthesis of vitamin D. Since sunlight is required to turn cholesterol into vitamin D, avoiding the sun will likewise undermine our ability to synthesize vitamin D.

Phytosterols are natural compounds structurally similar to mammalian cell-derived cholesterol. The best dietary sources of phytosterols are unrefined vegetable oils, seeds, cereals, nuts, and legumes.

Cholesterol and plant sterols are structurally similar, but undergo strikingly different metabolic fates in mammals. Phytosterol is a mixture of sterols i.e. a mixture of stigmasterol, beta-sitosterol, campesterol and stigmastenol, as shown in FIG. 1.

Figure 1

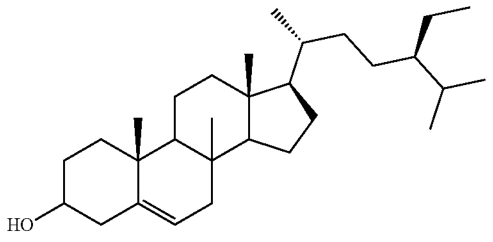

B-Sitosterol

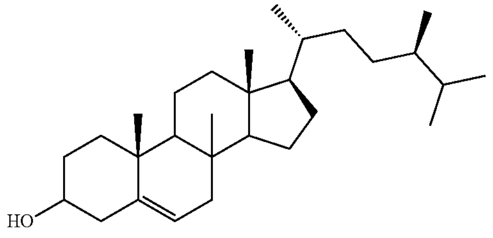

Campesterol

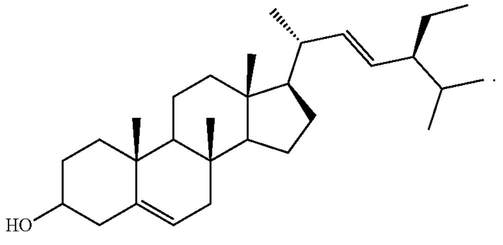

Stigmasterol

Stigmasterol is an unsaturated sterol, having one double bond in the sterol ring structure and one double bond in the side chain. Beta sitosterol is an unsaturated sterol with one double bond in sterol ring structure. Campesterol is structurally similar to beta sitosterol but has methyl group substituent at C24 position instead of an ethyl group. Stigmastenol is a saturated sterol both in ring structure and in the side chain.

U.S. Pat. No. 3,920,531A discloses a process for the production of hydroxylated derivatives of cholesterol and 7-dehydrocholesterol which comprises subjecting a saturated unsubstituted or substituted derivative of cholestane, dissolved in a suitable solvent, in the presence of peracetic acid, to irradiation with ultraviolet radiation having a wavelength less than 350 mu, separating the reaction products, which if desired, are converted to other derivatives, and recovering the residue of the starting material.

U.S. Pat. No. 3,822,254 discloses a process for the preparation of 25-hydroxycholesterol and its esters starting from the naturally occurring (readily available and inexpensive) starting material, stigmasterol which is isolated commercially from Soybeans. The synthesis encompasses, as key steps, the protection of the 3-hydroxy-delta 5-function by formation of an i-steroid, cleavage of the 22, 23-double bond, and introduction of the properly substituted 5-carbon fragment to afford the 25-hydroxycholesterol side chain.

Synthesis of cholesterol from methods such as Robinson synthesis and Woodward synthesis are well reported. WO2016096989A1 discloses method of extracting cholesterol from fish oil, especially from fish oil waste residue by saponification followed by extraction with at least one non-water miscible solvent, at a temperature of above 30° C.

U.S. Pat. No. 5,128,162A discloses methods for removing cholesterol from edible oils.

WO1995014032A1 discloses a process for producing a 25-hydroxycholesterol by hydroxylating a cholesterol at the 25-position using a ruthenium compound as a catalyst.

WO2016096988 discloses method of extracting cholesterol from milk fat. Synthesis of vitamin D3 from various sources are reported in the prior art. However, there is no report for the synthesis of cholesterol and vitamin D3 from phytosterols as source.

Therefore, it is an objective of the present invention to provide a robust synthesis for the manufacture of cholesterol and vitamin D3 starting from an inexpensive source, i.e., naturally occurring phytosterols.

SUMMARY OF THE INVENTION

In line with the above objective, the present invention provides a synthetic process for commercial manufacture of Vitamin D3 from phytosterols.

Accordingly, the synthetic process for commercial manufacture of Vitamin D3 from phytosterols, which comprises;

a) Tosylating Phytosterol by treating with p-toluene sulfonyl halide in a base to obtain phytosteryl tosylate (1);

b) Treating the phytostery tosylate with methanol in a base to obtain Phytosteryl-1-methyl ether (2);

c) Treating the phytosteryl-i-methyl ether with ozonized oxygen in a solvent at a temperature range of −50 to −90° C. followed by treatment with reducing agent at a temperature range of −40° C. to 0° C. to obtain (20S)-20-hydroxymethyl-6β-methoxy-3α,5-cyclo-5α-pregnane (3);

d) Tosylating the (20S)-20-hydroxymethyl-6β-methoxy-3α,5-cyclo-5α-pregnane with a tosylating agent in a base to obtain (20S)-6β-methoxy-20-(p-toluene sulfonoxy methyl)-3α,5-cyclo-5α-pregnane (4);

e) Subjecting the (20S)-6β-methoxy-20-(p-toluene sulfonoxy methyl)-3α,5-cyclo-5α-pregnane to Grignard reaction by treatment with isopentyl bromide in an ether solvent in presence of CuBr·Me2S catalyst to obtain i-Cholesteryl methyl ether (5);

f) hydrolysing the i-Cholesteryl methyl ether in aq. Dioxane with catalytic amounts of PTSA at a temperature of 70-90° C. to obtain cholesterol (6) followed by converting into cholesterol acetate (7) by treatment with acetic anhydride in presence of a base at a temperature range of 30 to 70° C.;

g) Subjecting the cholesterol acetate to bromination by treating with a brominating agent in a hydrocarbon solvent to obtain 7-Bromo cholesteryl acetate followed by treating with TBAF in an ether solvent at a temperature range of 10 to 30° C. to obtain 7-dehydrocholesterol acetate;

h) subjecting the 7-dehydrocholesterol acetate to alkaline hydrolysis in an alcoholic solvent at about 30 to 60° C. to obtain 7-dehydrocholesterol (8); and i) Converting 7-dehydrocholesterol into vitamin D3 by irradiating under high-pressure mercury lamp in a solvent in presence of sensitizer.

In another aspect, the present invention provides a synthetic process for commercial manufacture of cholesterol from phytosterols.

Accordingly, the synthetic process for commercial manufacture of cholesterol from phytosterols, which comprises;

a) Tosylating Phytosterol by treating with p-toluene sulfonyl halide in a base to obtain phytosteryl tosylate (1);

b) Treating the phytostery tosylate with methanol in a base to obtain Phytosteryl-1-methyl ether (2);

c) Treating the phytosteryl-i-methyl ether with ozonized oxygen in a solvent at a temperature range of −50 to −90° C. followed by treatment with reducing agent at a temperature range of −40° C. to 0° C. to obtain (20S)-20-hydroxymethyl-60-methoxy-3α,5-cyclo-5α-pregnane (3);

d) Tosylating the (20S)-20-hydroxymethyl-6β-methoxy-3α,5-cyclo-5α-pregnane with a tosylating agent in a base to obtain (20S)-6β-methoxy-20-(p-toluene sulfonoxy methyl)-3α,5-cyclo-5α-pregnane (4);

e) Subjecting the (20S)-60-methoxy-20-(p-toluene sulfonoxy methyl)-3α,5-cyclo-5α-pregnane to Grignard reaction by treatment with isopentyl bromide in an ether solvent in presence of CuBr·Me2S catalyst to obtain i-Cholesteryl methyl ether (5);

f) hydrolysing the i-Cholesteryl methyl ether in aq. Dioxane with catalytic amounts of PTSA at a temperature of 70-90° C. to obtain cholesterol (6).

DETAILED DESCRIPTION

The invention will now be described in detail in connection with certain preferred and optional embodiments, so that various aspects thereof may be more fully understood and appreciated.

The present invention provides a synthetic process for commercial manufacture of Vitamin D3 from phytosterols.

Phytosterols are globally manufactured by various companies such as ADM, Cargill, BASF, Raisio, DuPont, Arboris, PrimaPharm, FenchChem, DRT and Lipofoods. The phytosterols samples used to carry out the present invention is sourced from USA, Germany and Bangladesh.

Accordingly, the synthetic process for commercial manufacture of Vitamin D3 from phytosterols, which comprises;

a) Tosylating Phytosterol by treating with p-toluene sulfonyl halide in a base to obtain phytosteryl tosylate (1);

b) Treating the phytostery tosylate with methanol in a base to obtain Phytosteryl-1-methyl ether (2);

c) Treating the phytosteryl-i-methyl ether with ozonized oxygen in a solvent at a temperature range of −50 to −90° C. followed by treatment with reducing agent at a temperature range of −40° C. to 0° C. to obtain (20S)-20-hydroxymethyl-6β-methoxy-3α,5-cyclo-5α-pregnane (3);

d) Tosylating the (20S)-20-hydroxymethyl-6β-methoxy-3α,5-cyclo-5α-pregnane with a tosylating agent in a base to obtain (20S)-6β-methoxy-20-(p-toluene sulfonoxy methyl)-3α,5-cyclo-5α-pregnane (4);

e) Subjecting the (20S)-60-methoxy-20-(p-toluene sulfonoxy methyl)-3α,5-cyclo-5α-pregnane to Grignard reaction by treatment with isopentyl bromide in an ether solvent in presence of CuBr·Me2S catalyst to obtain i-Cholesteryl methyl ether (5);

f) hydrolysing the i-Cholesteryl methyl ether in aq. Dioxane with catalytic amounts of PTSA at a temperature of 70-90° C. to obtain cholesterol (6) followed by converting into cholesterol acetate (7) by treatment with acetic anhydride in presence of a base at a temperature range of 30 to 70° C.;

g) Subjecting the cholesterol acetate to bromination by treating with a brominating agent in a hydrocarbon solvent to obtain 7-Bromo cholesteryl acetate followed by treating with TBAF in an ether solvent at a temperature range of 10 to 30° C. to obtain 7-dehydrocholesterol acetate;

h) subjecting the 7-dehydrocholesterol acetate to alkaline hydrolysis in an alcoholic solvent at about 30 to 60° C. to obtain 7-dehydrocholesterol (8); and i) Converting 7-dehydrocholesterol into vitamin D3 by irradiating under high-pressure mercury lamp in a solvent in presence of sensitizer.

The reaction of step a) can be conducted from room temperature to reflux temperature of the solvent.

The base used in steps a); step b); step d); step f) is an organic base such as pyridine, triethyl amine or DMAP or an inorganic base such as alkali or alkaline earth metals hydroxides, carbonates or bicarbonates. In a preferred embodiment, the base is an organic base selected from pyridine, triethyl amine or DMAP.

The phytosteryl tosylate obtained in step a) is a mixture of stigmasteryl tosylate, sitosteryl tosylate, and campesteryl tosylate.

The reaction of step b) can be conducted at a temperature range of 40° C. to reflux temperature of the solvent used.

The phytosteryl i-methyl ether obtained step b) is a mixture of stigmasteryl-1-methyl ether, sitosteryl-1-methyl ether and campesteryl-1-methylether.

The solvent used in step c) is selected from methylene chloride, ethylene chloride, methanol, ethanol, isopropanol, water or mixtures thereof. In a preferred embodiment, the solvent is a mixture of methylene chloride and methanol.

The reducing agent used in step c) is selected from sodium borohydride, lithium aluminium hydride, sodium hydride etc.

In an embodiment, after isolation of (20S)-20-hydroxymethyl-6β-methoxy-3α,5-cyclo-5α-pregnane (3) obtained in step c) using column chromatography, the fractions containing sitosterol-i-methyl ether are heated in aqueous dioxane in presence of catalytic PTSA at 100° C. for 2 h, followed by removal of solvent and crystallization in methanol to yield phytosterol as colourless solid which is free from stigmasterol.

The p-toluene sulfonyl halide in step a) and step d) is selected from p-toluene sulfonyl chloride, p-toluene sulfonyl bromide and p-toluene sulfonyl iodide.

The tosylating in step d) may be conducted at a temperature range of −5 to 5° C. The reaction in step e) may be conducted at a temperature range of 40 to 70° C. The ether solvent used in step e) and step g) is selected from diethylether, diisopropylether or THF.

The brominating agent used in step g) is selected from bromine, NBS or DDH (1,3-dibromo-5,5-dimethyl hydantoin and the hydrocarbon solvent is pet ether.

In an embodiment, since the 7-bromo cholesterol acetate is unstable; directly used as such for next reaction without isolation or further purification.

The alcoholic solvent in step h) is selected from methanol, ethanol and isopropanol.

The solvent in step i) is selected from an alcoholic solvent like methanol, ethanol, isopropanol; ethers such as diethylether, diisopropylether, THF; esters such as ethylformate, ethylacetate etc.; nitriles such as acetonitrile etc. and hydrocarbon solvents such as methylenechloride, ethylenedichloride, chloroform, benzene, toluene etc.

The sensitizer used in step i) is selected from 5-(3-pyridyl)-2,2'-bithiophene, 2,5-Di(Pyridin-3-yl) thiophene; 2,5-diphenyl thiophene; 5-(2-Pyridyl)-2,2'-Bithiophene; 5-(4-Pyridyl)-2,2'-Bithiophene; 2-Phenyl-5-(2-Pyridyl) Thiophene; 2-Phenyl-5-(3-Pyridyl)-Thiophene; 2-Phenyl-5-(4-Pyridyl)-Thiophene; 2,2'-5',2"-Terthiophene; and 2,5-Di (2-thienyl) Furane.

In yet another preferred embodiment, the invention provides method of irradiation of 7-dehydrocholesterol, which method comprises;

a) Irradiating 7-dehydrocholesterol in a solvent with a high-pressure mercury lamp;

b) Adding a sensitizer to convert tachysterol formed during the irradiation into preD3;

c) Concentrating and storing the irradiated solution at ≤−10° C. overnight to crystallize the non-converted 7-dehydrocholesterol followed by filtrating the same;

d) Dissolving the concentrated filtrate in an organic solvent followed by heating to obtain cholecalciferol; and e) Purifying the cholecalciferol from mixture of acetone and water.

The solvent used in step a) may be selected from an alcoholic solvent like methanol, ethanol, isopropanol; ethers such as diethylether, diisopropylether, THF; esters such as ethylformate, ethylacetate etc.; nitriles such as acetonitrile etc. and hydrocarbon solvents such as methylenechloride, ethylenedichloride, chloroform, benzene, toluene etc.

The sensitizer used in step i) is selected from 5-(3-pyridyl)-2,2'-bithiophene, 2,5-Di(Pyridin-3-yl) thiophene; 2,5-diphenyl thiophene; 5-(2-Pyridyl)-2,2'-Bithiophene; 5-(4-Pyridyl)-2,2'-Bithiophene; 2-Phenyl-5-(2-Pyridyl) Thiophene; 2-Phenyl-5-(3-Pyridyl)-Thiophene; 2-Phenyl-5-(4-Pyridyl)-Thiophene; 2,2'-5',2"-Terthiophene; and 2,5-Di (2-thienyl) Furane.

The organic solvent in step d) may be a hydrocarbon or halogenated hydrocarbon. Preferably, the organic solvent is hydrocarbon, more preferably toluene.

In another aspect, the present invention provides a synthetic process for commercial manufacture of cholesterol from phytosterols.

Accordingly, the synthetic process for commercial manufacture of cholesterol from phytosterols, which comprises;

a) Tosylating Phytosterol by treating with p-toluene sulfonyl halide in a base to obtain phytosteryl tosylate (1);

b) Treating the phytostery tosylate with methanol in a base to obtain Phytosteryl-1-methyl ether (2);

c) Treating the phytosteryl-i-methyl ether with ozonized oxygen in a solvent at a temperature range of −50 to −90° C. followed by treatment with reducing agent at a temperature range of −40° C. to 0° C. to obtain (20S)-20-hydroxymethyl-6β-methoxy-3α,5-cyclo-5α-pregnane (3);

d) Tosylating the (20S)-20-hydroxymethyl-6β-methoxy-3α,5-cyclo-5α-pregnane with a tosylating agent in a base to obtain (20S)-6β-methoxy-20-(p-toluene sulfonoxy methyl)-3α,5-cyclo-5α-pregnane (4);

e) Subjecting the (20S)-6β-methoxy-20-(p-toluene sulfonoxy methyl)-3α,5-cyclo-5α-pregnane to Grignard reaction by treatment with isopentyl bromide in an ether solvent in presence of CuBr·Me2S catalyst to obtain i-Cholesteryl methyl ether (5);

f) hydrolysing the i-Cholesteryl methyl ether in aq. Dioxane with catalytic amounts of PTSA at a temperature of 70-90° C. to obtain cholesterol (6).

The reaction of step a) can be conducted from room temperature to reflux temperature of the solvent.

The base used in steps a); step b); step d); step f) is an organic base such as pyridine, triethyl amine or DMAP or an inorganic base such as alkali or alkaline earth metals hydroxides, carbonates or bicarbonates. In a preferred embodiment, the base is an organic base. The preferred base is pyridine or DMAP.

The reaction of step b) can be conducted at a temperature range of 40° C. to reflux temperature of the solvent used.

The solvent used in step c) is selected from methylene chloride, ethylene chloride, methanol, ethanol, isopropanol, water or mixtures thereof. In a preferred embodiment, the solvent is a mixture of methylene chloride and methanol.

The reducing agent used in step c) is selected from sodium borohydride, lithium aluminium hydride, sodium hydride etc.

The p-toluene sulfonyl halide in step a) and step d) is selected from p-toluene sulfonyl chloride, p-toluene sulfonyl bromide and p-toluene sulfonyl iodide.

The tosylating in step d) may be conducted at a temperature range of −5 to 5° C. The reaction in step c) may be conducted at a temperature range of 40 to 70° C.

The ether solvent used in step e) is selected from diethylether, diisopropylether or THF.

Synthesis of Cholesterol/Vitamin D3 from phytosterol according to the present invention is shown in scheme 3.

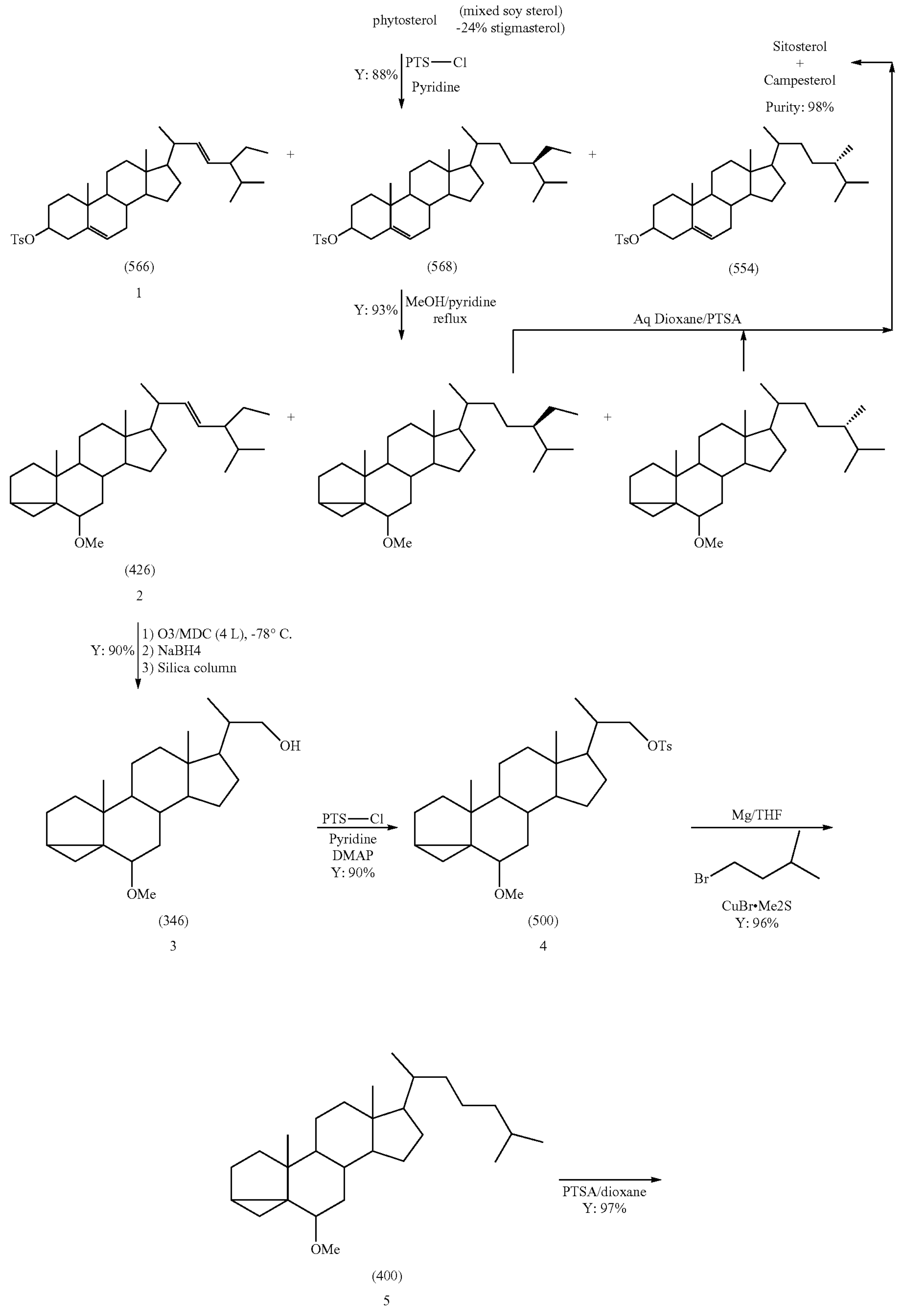
phytosterol (mixed soy sterol) -24% stigmasterol)
Y: 88%
PTS—Cl
Pyridine
Sitosterol
+
Campesterol
Purity: 98%
TsO
TsO
TsO
(566)
1
(568)
(554)
Y: 93%
MeOH/pyridine
reflux
Aq Dioxane/PTSA
OMe
OMe
OMe
(426)
2
Y: 90%
1) O3/MDC (4 L), -78° C.
2) NaBH4
3) Silica column
OH
OTs
PTS—Cl
Pyridine
DMAP
Y: 90%
Mg/THF
Br
CuBr•Me2S
Y: 96%
OMe
OMe
(346)
3
(500)
4
OMe
PTSA/dioxane
Y: 97%
(400)
5

-continued

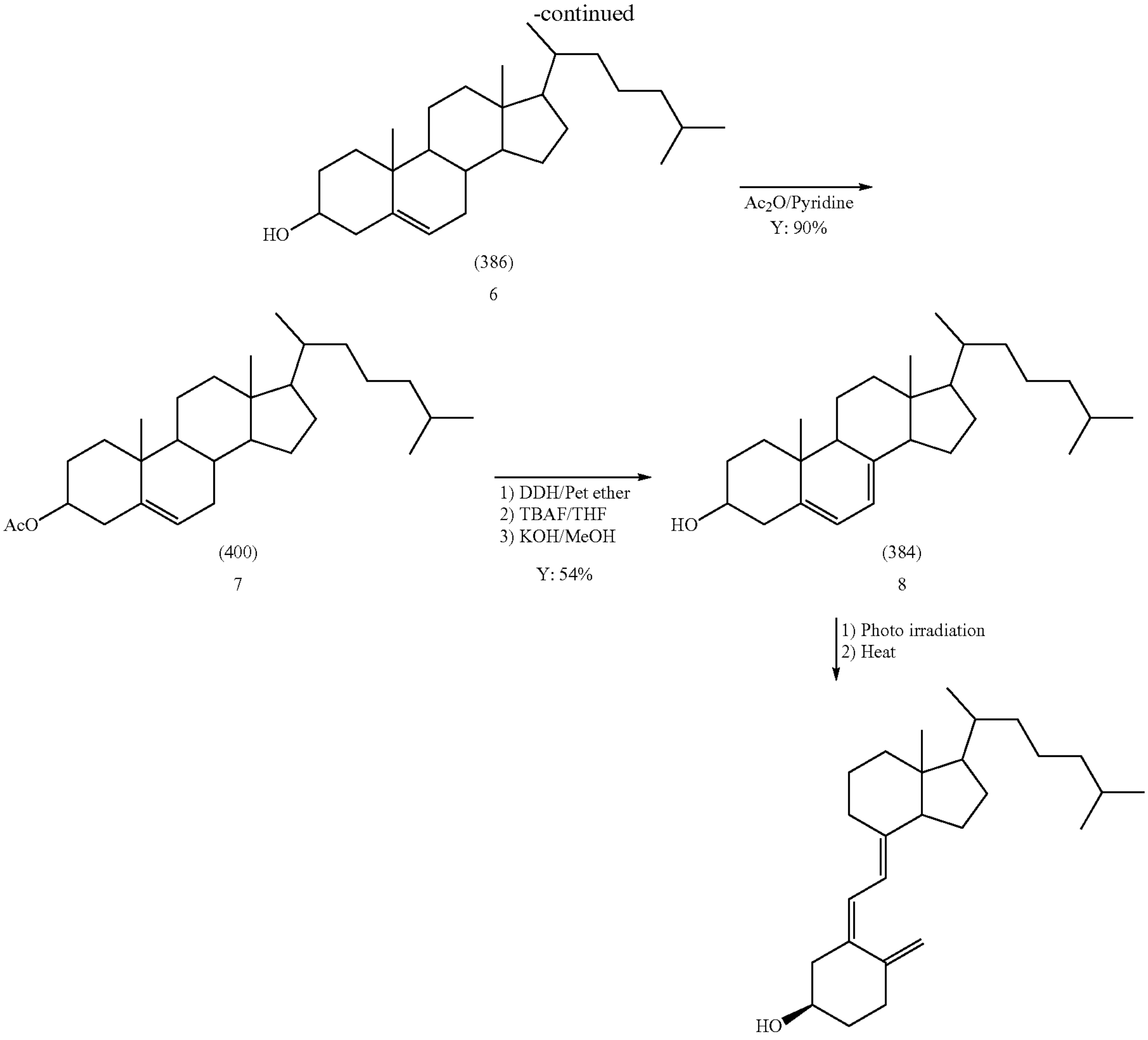

(386) 6

(400) 7

(384) 8

Cholecalciferol

The present invention is exemplified by the following examples which are provided for illustration only and, should not be construed to limit the scope of the invention.

Example 1

Preparation of Phytosteryl Tosylate (1)

To a solution of 500.0 g (1.20 mol) of Phytosterol in 5000 ml of dry pyridine was added 500.0 g (2.62 mol) of p-toluene sulfonyl chloride and the mixture was stirred at 25° C. for 16 hrs. Pyridine was removed by vacuum distillation and the residue was slowly poured into 10% sodium carbonate solution. The precipitated product was collected by filtration, washed with water followed by methanol and dried in vacuum overnight to yield 600.0 g. of phytosteryl tosylate, which was used for next step without further purification.

Yield: 600 g (88 %)

Appearance: White solid

GC analysis: Stigmasteryl tosylate: 20.37% (RT: 6.10)

Sitosteryl tosylate: 42.29%(RT:6.80)

Campesteryl tosylate: 15.60%(RT25.76)

Example 2

Preparation of Phytosteryl-i-Methyl Ether (2)

A mixture of 600.0 g (1.06 mol) of phytostery tosylate in 5500 ml of methanol and 300 g (3.79 mol) of pyridine was stirred at 55° C. for 5 hrs. The cooled solution was concentrated under reduced pressure. The residue was poured into water and extracted with dichloromethane. The dichloromethane solution was dried over anhydrous sodium sulfate and evaporated to dryness to yield 420.0 g. of colorless thick oil, which was used for next step without further purification.

Yield: 420 g (93 %)

Appearance: colorless thick oil

GC analysis: Stigmasteryl-i-methyl ether: 19.49% (RT: 5.47)

Sitosteryl-i-methyl ether: 48% (RT 6.05)

Campesteryl-methylether: 15.08% (RT: 6.34)

Example 3

Preparation of (20S)-20-hydroxymethyl-6β-methoxy-3α,5-cyclo-5α-pregnane

A solution of 420.0 g (0.98 mol) of phytosteryl-i-methyl ether in 4000 ml of methylene chloride and 1300 ml of methanol was cooled to −78° C. and treated with ozonized oxygen for 3-4 h. The reaction vessel was flushed with nitrogen and 42 g (1.11 mol) of sodium borohydride was added. The mixture was stirred at −50° C. for 1 h and then allowed to warm to 0° C. over a 1 h period. Water was added slowly to decompose the excess hydride and the product was extracted with methylene chloride. The methylene chloride solution was washed with brine solution. The methylene chloride solution was then dried over anhydrous sodium sulfate and evaporated to dryness. The 400 g of crude reaction mass was purified by column chromatography using silica gel to get 60.0 g. of (20S)-20-hydroxy methyl-6β-methoxy-3α,5-cyclo-5α-pregnane.

Yield: 60 g (90%)

Appearance: colorless solid

GC analysis: 93.6% purity (RT 3.35)

Fractions containing sitosterol-i-methyl ether collected separately and concentrated to get thick oil which upon heating in aqueous dioxane in presence of catalytic PTSA at 100° C. for 2 h, followed by removal of solvent and crystallization in methanol gave 230 g of colourless solid as phytosterol free from stigmasterol.

Yield: 60 g (90 %)

Appearance: colorless solid

GC analysis: >95% purity

Example 4

Preparation of (20S)-6β-methoxy-20-(p-toluene sulfonoxy methyl)-3α,5-cyclo-5α-pregnane (4)

To a solution of 60 g (0.172 mol) of (20S)-20 hydroxymethyl-6β-methoxy-3α,5-cyclo-5α-pregnane in 600 ml. of pyridine was added slowly 60 g. (0.314 mol) of p-toluene sulfonyl chloride at 0° C. The mixture was stirred at 0° C. for 5 h. Several chips of ice were added, and the mixture was stirred for 5 minutes to decompose the excess p-toluene sulfonyl chloride. The mixture was poured into water and the product was extracted with methylene chloride. The methylene chloride solution was washed with water and brine solution. The solution was dried over anhydrous sodium sulfate and evaporated to dryness to yield 78.0 g white solid of (20S)-6β-methoxy-20-(p-toluene sulfonoxy methyl)-3a, 5-cyclo-5α-pregnane, which was used for next step without further purification.

Yield: 78 g (90%)

Appearance: colorless solid

Example 5

Preparation of i-Cholesteryl methyl ether (5)

To stirred magnesium turnings (54.0 g, 2.25 mol) in THF (750 ml) few drops of 1,2-dibromoethane were added under Nitrogen atmosphere followed by few drops of isopentyl bromide and heated to 50° C. for few minutes to initiate reaction then a remaining solution of isopentyl bromide (78.0 g, 0.51 mol) was added drop wise under N2. After being stirred at the same temperature of 50° C. for 60 min, the reaction mixture was cooled at 0° C. and a suspension of CuBr·Me2S (4.0 g, 0.01 mol) was added and a solution of (20S)-6β-methoxy-20-(p-toluene sulfonoxy methyl)-3α,5-cyclo-5α-pregnane (4) (78 g, 0.156 mol) in THF (300 mL) was added drop wise at 0° C. under N2. After being stirred at room temperature for 2-3 h, the reaction mixture was poured into saturated aqueous NH4Cl at 0° C. and the aqueous layer was extracted twice with EtOAc. The combined organic layer was washed with saturated aqueous NH4Cl and brine and dried over Na2SO4. The obtained mixture was filtered and concentrated in vacuo. The solid product obtained was stirred in methanol at room temperature for 30 min filtered and dried under vacuum to get white solid of IME cholesterol.

Yield: 60 g (96%)

Appearance: White solid

GC analysis: 94.97% (RT: 5.09)

Example 6

Preparation of Cholesterol (6)

The i-cholesteryl methyl ether 60 g (0.15 mol) was dissolved in aqueous dioxane (9:1) 600 mL and heated at 80° C. in presence of catalytic PTSA until completion of starting material (~3 h). Aqueous work up of reaction mixture, followed by extraction with ethyl acetate and removal of solvent yielded cholesterol. Crystallization was carried out in methanol gave cholesterol as white solid (56 g).

Yield: 56 g (97%)

Appearance: White solid

M.pt: 149° C.

$[\alpha]^{D}_{20}$: −34° (C=:2, CHC13)

HPLC analysis: 99.-l7(RT: 14.22)

GC analysis: 99.03(RT: 7.59)

IR(Neat): 3481,2933,2866,1466,1337,1056,839,799,594,

1HNMR (400MHz, CDC13): δ 5.35 (m, 1H), 3.55 (m, 1H), 0.94 (s, 3H), 0.94 (d, J =4.9 Hz, 3H), 0.87 (d,J =6.4 Hz, 3H), 0.87 (d, J=6.8 Hz, 3H), 0.67 (s, 3H)

13C NMR (400 MHz, CDC13): 140.7,121.6,71.7,56.7,56.1,50.1,42.3,42.2,39.7,39.5,37.2, 36.4,36.1,35.7,31.8,31.6,28.2,27.9,24.2 23.8,22.8,22.5,21.0, 19.3,18.7,11.8.

Example 7

Preparation of Cholesterol Acetate (7)

Cholesterol (56 g, 0.145 mol) was suspended in petroleum ether (400 mL) followed by addition of acetic anhydride (31.36 g, 0.30 mol) and DMAP (20.0 g, 0.163 mol) at room temperature and stirred at 40-60° C. for 2-4 h until completion of starting material. Reaction mixture was washed with water (50 mL×2) followed by saturated salt solution (100 mL), followed by (50 mL×2) 10% sodium bicarbonate solution and finally with water, dried the solvent over anhydrous Na2SO4 and removed the solvent to get white solid, which upon crystallization in methanol gave pure cholesterol acetate as white solid (56 g).

Yield: 56g (~90%)

M.Pt: 111-114°C.

$[\alpha]^{D}_{20}$: −44° C. (c=2, CHC13)

Appearance: White solid.

HPLC analysis: >95%

Example 8

Preparation of 7-Dehydrocholesterol (8)

To a stirred solution of cholesterol acetate (50 g 0.11 mole) in 500 mL pet ether was added DDH (1,3-dibromo- 5,5-dimethyl hydantoin, (16.4 g, 0.057 mole) followed by catalytic perkadox as initiator. Reaction mixture was heated to reflux at 65° C., until completion of starting material, monitored by TLC and HPLC. Reaction was quenched by adding water and extracted with pet ether, washed the pet ether layer with water, dried the pet ether layer over anhydrous Na2SO4 and removed the solvent to get crude 7-bromo cholesterol acetate as a pale yellow thick oil (~50 g), used as such for next reaction without further purification. To a stirred cooled solution of 7-Bromo cholesteryl acetate (50 g, 0.176 mole) in dry THF (200 mL) was added anhydrous TBAF (100 g, 0.317 mole) dissolved in dry THF (400 mL). Stirred the reaction mixture at 20° C. for 2 h. Reaction was monitored by HPLC. Reaction was quenched by adding water and extracted with ethyl acetate (3×200 mL). Washed the ethyl acetate layer with brine solution (200 mL) and dried over anhydrous Na2SO4 and removed the solvent to get crude as colourless solid, stirred with methanol and filtered the solid, dried and used for saponification step.

Yield: 30 g

7-Dehydrocholesterol acetate (30 g, 0.07 mole) was suspended in methanol (300 mL) and KOH (20 g, 0.36 mole) added and heated the reaction mixture at 45° C. for 2 h. Reaction was monitored by TLC. Solvent removed by distillation and added water to residual mass and extracted with dichloromethane. Dichloromethane layer washed with brine and dried over anhydrous Na2SO4, filtered and solvent removed to get crude product, crystallized in methanol/acetone to get pure 7-dehydrocholesterol as white solid (23 g).

Yield: 23 g (54 %, after two steps))

M.pt: 145° C.

Appearance: White solid $[\alpha]^{27}_{D}$=−12° (c=1, CHC13)

HPLC analysis: 96.5%(RT:11.13)

GC analysis: 98.5% (RT: 7.44)

1H NMR (400 MHz, CDC13):

δ 5.57 (m, 1H), 5.39(m, 1H), 3.66 (m, 1H), 0.94 (s, 3H), 0.94 (d, J =4.9 Hz, 3H), 0.87 (d,J =6.4 Hz, 3H), 0.87 (d, J =6.8 Hz, 3H), 0.61 (s, 3H)

13C NMR (400 MHz, CDC13): 141.1,139.7,1 19.6,1 16.2,70, 4,55.9,54.5,46.2,42.9,40.7,39.5,39.2,38.3,37.0,36. 1,36, 1,31.9,28.0,28.0,23.8,23.0,22.8,22.5,21.1,18.8,16.2, 11.8.

Example 9

Preparation of Vitamin D3 (Cholecalciferol)

In a 1.5 litre tetrahydrofuran was dissolved 46.8 g of 7-dehydro cholesterol of example 8, and the mixture was stirred in a magnetic stirrer under nitrogen atmosphere. To the mixture was added 1 g of butylated hydroxy toluene (BHT). During the irradiation, besides pre D3, tachysterol also formed, hence 1 g of sensitizer 5-(3-pyridyl)-2,2'-bithiophene was added to convert the formed tachysterol into preD3 and stirred for a while to obtain clear solution. Falling film apparatus was used to irradiate the solution continuously for 180 minutes at room temperature and the irradiation was carried out using ultra violet rays from the high pressure mercury lamp of wave length 250-360 nm. The content of the previtamin D derivative of intended product was determined and monitored by high performance liquid chromatography (HPLC). After 180 minute irradiation reaction mixture was cooled to 0-5° C. for 30 minutes. The solid separated out was filtered as first crop containing 7-Dehydrocholesterol (50-60%). The filtrate was concentrated to 20% of the original volume, cooled to 0-5° C. for 24 hrs and the separated solid was filtered as second crop that contained 7-Dehydrocholesterol (15-20%).

The first and second crops were combined and reused in subsequent batches. The filtrate was then evaporated under vacuum at 40-45° C. to get the crude compound which was then dissolved in 200 mL toluene and refluxed for 1-2 hr. The solvent was concentrated completely under vacuum to get crude reddish orange sticky mass (resin). Yield: 20 g The residue was purified by column chromatography over silica gel with Toluene: methyl ketone 1:99, 2:98, 4:96 & 5:95 to isolate pure Vitamin D3/cholecalciferol crystals which were recrystallized in acetone/water twice, filtered and dried to get highly pure crystals of Cholecalciferol The HPLC analysis of the vitamin D3 crystals are shown in Table 1 as shown below.

TABLE 1

| S no | Compound | % by HPLC | Potency |
|---|---|---|---|
| 1 | Vitamin $D_3$/Cholecalciferol | 98-99.5% | 40 MIU |
| 2 | 7-Dehydrocholesterol | ND | NA |
| 3 | Tachysterol | 0.01% | NA |
| 4 | Lumisterol | 0.01% | NA |
| 5 | Trans Vitamin $D_3$ | 0.05% | NA |

We claim:

1. A process for manufacture of cholesterol from phytosterols, which comprises;

treating a phytosterol with a p-toluene sulfonyl halide in a first base to obtain a phytosteryl tosylate;

treating the phytosteryl tosylate with methanol in a second base to obtain a phytosteryl-i-methyl ether;

treating the phytosteryl-i-methyl ether with ozonized oxygen in a first solvent at a temperature range of −50° C. to −90° C., followed by treatment with a reducing agent at a temperature range of −40° C. to 0° C. to obtain (20S)-20-hydroxymethyl-6β-methoxy-3α,5-cyclo-5α-pregnane;

tosylating the (20S)-20-hydroxymethyl-6β-methoxy-3α,5-cyclo-5α-pregnane with a tosylating agent in a third base to obtain (20S)-6-methoxy-20-(p-toluene sulfonoxy methyl)-3α,5-cyclo-5α-pregnane;

subjecting the (20S)-6-methoxy-20-(p-toluene sulfonoxy methyl)-3α,5-cyclo-5α-pregnane to a Grignard reaction by treatment with a reaction product of magnesium and isopentyl bromide in a first ether solvent in the presence of a $CuBr{\cdot}Me_2S$ catalyst to obtain i-cholesteryl methyl ether; and hydrolyzing the i-cholesteryl methyl ether in aqueous dioxane with catalytic amounts of PTSA at a temperature of 70-90° C. to obtain cholesterol.

2. The process as claimed in claim 1, wherein the step of treating a phytosterol with a p-toluene sulfonyl halide is carried out in a second solvent at a temperature ranging from room temperature to a reflux temperature of the second solvent.

3. The process as claimed in claim 1, wherein:

the step of hydrolyzing the i-cholesteryl methyl ether is carried out in the presence of a fourth base; and the first base, the second base, the third base, and the fourth base are each selected from the group consisting of:

an organic base selected from the group consisting of pyridine, triethyl amine and DMAP;

an inorganic base selected from the group consisting of alkali or alkaline earth metal of hydroxide, carbonate, and bicarbonate salts; and a mixture thereof.

4. The process as claimed in claim 1, wherein the step of treating the phytosteryl tosylate with methanol is carried out in a third solvent at a temperature ranging from 40° C. to a reflux temperature of the third solvent.

5. The process as claimed in claim 1, wherein:

the first solvent is selected from the group consisting of methylene chloride, ethylene chloride, methanol, ethanol, isopropanol, water, and a mixture thereof; and the reducing agent used is selected from the group consisting of sodium borohydride, lithium aluminium hydride, and sodium hydride.

6. The process as claimed in claim 1, wherein the p-toluene sulfonyl halide and the tosylating agent are each selected from the group consisting of p-toluene sulfonyl chloride, p-toluene sulfonyl bromide, and p-toluene sulfonyl iodide.

7. The process as claimed in claim 1, wherein the step of tosylating the (20S)-20-hydroxymethyl-6β-methoxy-3α,5-cyclo-5α-pregnane is conducted at a temperature ranging from −5° C. to 5° C.

8. The process as claimed in claim 1, wherein the step of subjecting the (20s)-6-methoxy-20-(p-toluene sulfonoxy methyl)-3α,5-cyclo-5α-pregnane to a Grignard reaction is conducted at a temperature range of 40° C. to 70° C.

9. The process as claimed in claim 1, wherein the first ether solvent is selected from the group consisting of diethylether, diisopropylether, THF, and mixtures thereof.

10. The process as claimed in claim 1, wherein the step of treating the phytosterol with the p-toluene sulfonyl halide produces a phytosteryl tosylate comprising a mixture of stigmasteryl tosylate, sitosteryl tosylate, and campesteryl tosylate.

11. The process as claimed in claim 10, wherein the step of treating the phytosteryl tosylate with methanol produces a phytosteryl-i-methyl ether comprising a mixture of stigmasteryl-1-methyl ether, sitosteryl-1-methyl ether and campesteryl-1-methylether.

* * * * *